United States Patent [19]

Covington et al.

[11] Patent Number: 4,491,587

[45] Date of Patent: Jan. 1, 1985

[54] TETRAZOLE DERIVATIVES

[75] Inventors: Robert R. Covington; Davis L. Temple, Jr., both of Evansville; Joseph P. Yevich, Newburgh, all of Ind.

[73] Assignee: Mead Johnson & Company, Evansville, Ind.

[21] Appl. No.: 167,552

[22] Filed: Jul. 11, 1980

Related U.S. Application Data

[62] Division of Ser. No. 903,265, May 5, 1978, Pat. No. 4,223,031.

[51] Int. Cl.$^3$ .......................................... C07D 257/04
[52] U.S. Cl. .................................. 424/269; 424/270; 548/161; 548/190; 548/198; 548/252; 548/254
[58] Field of Search ............... 548/190, 161, 198, 252, 548/254; 424/270, 269

[56] References Cited

U.S. PATENT DOCUMENTS

| | | | |
|---|---|---|---|
| 3,299,087 | 1/1967 | Spivack et al. | 548/190 |
| 3,538,086 | 11/1970 | Mair et al. | 260/239.75 |
| 3,689,488 | 9/1972 | Dukes | 544/263 |
| 3,888,983 | 6/1975 | Baetz | 424/251 |
| 4,014,917 | 3/1977 | Carter | 548/161 |
| 4,033,961 | 7/1977 | Schwender et al. | 544/252 X |
| 4,041,163 | 8/1977 | Biandra et al. | 424/251 |
| 4,072,679 | 2/1978 | Denzel et al. | 544/250 |
| 4,083,980 | 4/1978 | Schromm et al. | 424/251 |
| 4,122,274 | 10/1978 | Juby | 544/282 |
| 4,223,031 | 9/1980 | Covington et al. | 424/251 |

OTHER PUBLICATIONS

Ogura et al., Chem. Pharm. Bull. 21(9), 2019–2025 (1973).
Antaki et al., J. Chem. Soc. 551–555 (1951).
Dunwell et al., J. Chem. Soc. (C), 2084–2087 (1971).
Gompper et al., Chem. Ber. 95, 2871–2880 (1962).
Galasko et al., J. South African Chem. Inst. 22(2), 121–127 (1969).
Richardson, Jr. et al., J. Med. Chem. 15, 1203–1206 (1972).
Alaimo, J. Heterocyclic Chem. 10, 769–772 (1973).

*Primary Examiner*—Nicholas S. Rizzo
*Attorney, Agent, or Firm*—Robert H. Uloth; Richard P. Ryan

[57] ABSTRACT

6-(1H-Tetrazol-5-yl)thiazolo[3,2-a]pyrimidin-5-ones, 3-(1$\overline{H}$-tetrazol-5-yl)-4H-pyrimido[2,1-b]benzothiazol-4-ones, and the corresponding imidazo- and triazolo-pyrimidines, thiones, and imines are useful as antiallergy and antiasthmatic compounds by virtue of their inhibitory action on the immediate hypersensitivity reaction in mammals and relaxant action on the tracheal muscle. Intermediates in the synthesis of these substances from 2-aminoazoles and ethoxymethylene malononitrile also have smooth muscle relaxant and immediate hypersensitivity reaction inhibitory activity.

4 Claims, No Drawings

TETRAZOLE DERIVATIVES

REFERENCE TO RELATED APPLICATION

This application is a division of U.S. application Ser. No. 903,265 filed May 5, 1978 and now U.S. Pat. No. 4,223,031 patented Sept. 16, 1980.

FIELD OF THE INVENTION

This invention is concerned with pyrimidines having a fused azole ring such that a pyrimidine ring nitrogen atom is common to the two rings (Class 260, Subclass 251A). The ring systems involved are thiazolo[3,2-a]pyrimidine, [1,2,4]triazolo[1,5-a]pyrimidine, and imidazo[1,2-a]pyrimidine each of which may have a fused benzo ring as in the pyrimidino[2,1-b]benzothiazole ring system. The compounds are further characterized by a keto, thiono, or imino group in the pyrimidine ring position adjacent to the bridge-head nitrogen atom, and the acidic 5-tetrazolyl group in the position adjacent to the keto, thiono, or imino group. Various optional substituents may be present in the azole or benzazole ring.

DESCRIPTION OF THE PRIOR ART

Thiazolo[3,2-a]pyrimidinones and pyrimido[2,1-b]benzothiazolones have been previously described by Ogura, et al. Chem. Pharm. Bull., Tokyo, 21 (9), 2019-2025 (1973), Antaki, et al., J. Chem. Soc., 551 (1951), Baetz, U.S. Pat. No. 3,888,983 (June 10, 1975), Dunwell, et al., J. Chem. Soc. (C) 2094-2097 (1971), Gompper, et al., 95, 2871-2880 (1962), and Galasko, et al., So. Afr. Chem. Inst. 22(2) 121-127 (1969), but none of those references discloses a 1H-tetrazol-5-yl substituted compound.

A number of 3-carbalkoxy-4H-pyrimido[2,1-b]benzothiazol-4-ones have been investigated for anti-parasitic, anti-viral, and anti-microbial activity and the results described in the following references.

Mair, et al., U.S. Pat. No. 3,538,086 patented Nov. 3, 1970.

Richardson, Jr., et al., J. Med. Chem., 15, 1203-1206 (1972).

Alaimo, J. Hetero. Chem., 10, 769-772 (1973).

4-Oxo-N-(1H-tetrazol-5-yl)-4H-pyrimido[2,1-b]benzothiazol-3-carboxamide is disclosed by Bindra, et al., in U.S. Pat. No. 4,041,163 patented Aug. 9, 1977 as an anti-allergy agent.

SUMMARY OF THE INVENTION

The present invention is concerned with compounds having Formula I.

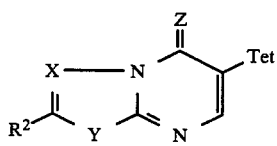

Formula I

Included in Formula I are compounds of Formulas Ia, Ib, and Ic.

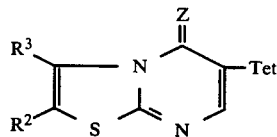

Formula Ia

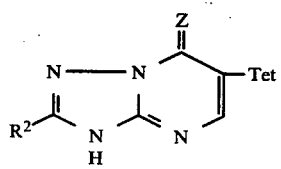

Formula Ib

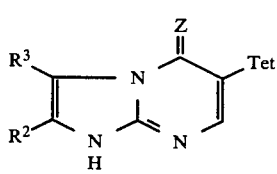

Formula Ic

In Formulas I, Ia, Ib, and Ic the symbols Tet, X, Y, Z, $R^2$, and $R^3$ have the following meanings.

Tet is 1H-tetrazol-5-yl;

X is N or $CR^3$,

Y is S or NH with the proviso that when Y is S, X is $CR^3$,

Z is O, S, or NH, $R^2$ and $R^3$ are independently selected from H, the substituent A, or taken together with the carbon atoms to which they are attached denote cycloalkenyl having 5 to 7 ring members and up to 2 ring substituents, benzo, monosubstituted benzo or disubstituted benzo wherein said substituents are defined by A, and A is selected from the group consisting of alkyl, alkenyl, alkynyl, alkoxy, alkenoxy, alkanoyl, alkenoyl, alkylsulfonyl, alkylsulfinyl, alkylthio, alkanoamido, cycloalkyl having 3 to 6 ring members and 1 to 3 optional alkyl substituents, cycloalkylalkyl having 3 to 6 ring members and 1 to 3 optional alkyl substituents, wherein each of the foregoing groups has up to 8 carbon atoms, phenyl, phenylmethyl, trifluoromethyl, nitro amino, hydroxyl, halogen, carbamoyl, cyano, and cyanoalkyl having from 2 to 4 carbon atoms.

The compounds of Formula I have utility as antiallergic agents. Some of them also have bronchodilator activity. They function as antiallergy agents by inhibition of the immediate hypersensitivity reaction. Preferred compounds are those wherein Z is oxo. Particularly preferred compounds are those of Formula Ia wherein Z is oxo, and $R^2$ and $R^3$ are independently selected from hydrogen and the substituent A as defined above.

Further particularly preferred compounds are those of Formula Ia wherein Z is oxo, and $R^2$ and $R^3$ together with the carbon atoms to which they are attached denote a fused benzo ring. Particularly preferred compounds are those of Formula Ia wherein Z is oxo, and $R^2$ and $R^3$ together with the carbon atoms to which they are attached denote a mono-substituted fused benzo ring wherein the substituent is selected from the group defined above with respect to A. Particularly preferred compounds are those of Formula Ia wherein Z is oxo, and $R^2$ and $R^3$ together with the carbon atoms to which they are attached denote the di-substituted fused benzo ring wherein the substituents are independently selected from the group defined above with respect to the letter A.

The preferred pyrimido[2,1-b]benzothiazoles of the types just referred to wherein $R^2$ and $R^3$ are joined to form the fused benzo ring may be described by Formula V.

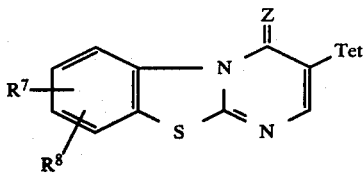

Formula V

In Formula V, $R^7$ and $R^8$ are independently selected from H and the substituent A, wherein A, Tet and Z have same meaning given with respect to Formula Ia.

The substances of Formula I inhibit the degranulation of sensitized mast cells. Immediate hypersensitivity reactions such as asthma, hay fever, allergic rhinitis, urticaria, and food allergy are believed to be mediated by reaction of immunoglobulin E, sometimes referred to as reaginic antibody with an antigen on the cell membrane of a mast cell to initiate reactions within the mast cell which ultimately release mediators such as bradykinin, histamine, serotonin, or slow reacting substance-A (SRS-A). The mediators effect changes in end organs such as airways, blood vessels, skin, and mucus membranes resulting in the symptoms of an allergic attack. The present substances are believed to prevent the release of mediators thereby preventing the allergic attack. They are, therefore, useful in the prophylactic treatment of subjects possessing hypersensitivities of the foregoing types, and inhibit acute allergic attacks such as an asthmatic attack.

Preferred compounds are distinguished particularly by the fact that they are orally active, have very low toxicities, have bronchodilator activity in addition to immediate hypersensitivity reaction inhibitory activity, and are substantially devoid of other types of pharmacologic action. They are of particular value for use prophylactically by hypersensitive subjects to prevent the manifestations of allergic reaction on exposure to an allergen for the hypersensitive condition.

Activity of test compounds in the passive cutaneous anaphylaxis reaction (PCA) in the rat has been shown in the prior art to correlate with the utility of active compounds in the treatment of immediate hypersensitivity conditions such as asthma. Rat reaginic antiserum is prepared substantially according to the method of Mota, Immunology, 7, 681–699 (1964) employing male Sprague-Dawley (Carworth Farms) or Wistar (Harlan) rats weighing 100–175 g. which are injected intramuscularly with a solution of egg albumin in saline at a dose of 10 mg. per kg. and intraperitoneally with $2 \times 10^{10}$ Bordetella pertussis organisms. Twelve days after injection, the serum is collected and the antibody titer is determined. The sera which contain sufficient antibody to cause a 10 mm. spot in the dorsal skin of the rat in the PCA test after a 10-fold dilution are pooled. The highest dilution of antiserum capable of inducing PCA in the rat 48 to 72 hrs. after injection is normally in the range of 50–80. The selected reaginic anti-sera are stored frozen until use.

For carrying out the test, groups of 5 to 10 male Sprague-Dawley (Carworth Farms) rats, each rat weighing 100–150 g., are used. Forty-eight hours prior to the test, the animals are passively sensitized by intradermal injection of 0.1 ml. of the above diluted antiserum at various locations on the shaved skin of the back. A dilution of antiserum is used so that a spot following challenge of 20–25 mm. in diameter is obtained. Challenge consists of an intravenous injection of 25 mg./kg. of body weight of egg albumin and a like amount of Evan's blue dye in saline. A higher dilution of the antiserum is injected in at least one location to allow a more sensitive measure of the activity of less potent compounds. A latent period of 48 hrs. is allowed before the animals are treated with the test drug administered by either intraperitoneal or intravenous injection or orally by gavage. Challenge as described above is given 15 min. subsequent to treatment with the test drug. The response to the antigen challenge in the sensitized localities on the skin is an increased capillary permeability and leakage of the blue dye into the area surrounding the sensitized site. The PCA response is scored by measuring the mean spot diameter on the excised and reversed skin 20–30 min. after challenge. In each experiment a group of control animals receiving no drug is employed. The percent inhibition of the PCA is calculated by determining the mean diameters of the spots in the control and treated animals and computing the difference between the squares of the mean diameters of the control animals and the treated animals and expressing this difference as a percentage of the square of the mean diameter of the control animals. Results are expressed as percent inhibition.

Various doses of test compound in parallel experiments are employed and a dose response curve is constructed for quantitative comparison of potencies among active compounds. The $ED_{50}$, the dose at which 50% inhibition of the PCA occurs, is determined by interpolation. In other modifications, various time intervals are allowed between drug treatment and challenge to ascertain the duration of drug effect.

The data in the following table are illustrative of the activity of a number of the present compounds in the rat PCA test.

| ANTIALLERGIC ACTION IN RATS | |
|---|---|
| Drug | PCA Response, ED 50 mg/kg |
| Example 33 | 57% @ 10, p.o.* |
| Example 23 | 2.9, p.o. |
| Example 24 | 0.064, p.o. |
| Example 24 | 0.0049, i.v. |
| Example 32 | 34.9% @ 25, p.o.* |
| Example 31 | 1.88, p.o. |
| Example 28 | 39% @ 25, p.o.* |
| Example 22 | 22.4% @ 10, p.o.* |
| Example 15 | 36.1% @ 10, p.o.* |

*percent inhibition at the dose specified.

The compound of Example 24 has an approximate $LD_{50}$ in the rat when treated orally within the range of 2,000 to 5,000 mg/kg of body weight. The substances of Examples 23, 24, 25, 28, 31, and 32 also cause relaxation of the spontaneous tonus of the guinea pig trachea in vitro which is suggestive of bronchodilator activity. The substance of Example 15 is inactive in the guinea pig tracheal spiral in vitro test.

The substances of Formula I are acids and form salts with bases. Salts with the pharmaceutically acceptable bases are preferred for medical purposes. Accordingly, the pharmaceutically acceptable metal, ammonium, and amine salts of substances of Formula I are included within the present invention. The pharmaceutically acceptable salts are obtained from pharmaceutically acceptable bases and a compound of Formula I, and are those in which the cation does not contribute significantly to the toxicity or pharmacological activity of the salt. They are the pharmacologic equivalents of the acids of Formula I. In some instances, the salts have physical properties which make them more desirable for pharmaceutical formulation purposes such as solubility, lack of hygroscopicity, compressibility with respect to tablet formation and compatibility with other ingredients with which the substances may be used for pharmaceutical purposes. The salts may be prepared by reaction of one of the substances of Formula I with a base preferably in solution in a reaction inert liquid medium or they can be prepared by metathesis or treatment with an ion exchange resin under conditions wherein the cation of one salt of substance of Formula I is replaced by another cation and the undesired species is eliminated, for instance by precipitation from solution or extraction into a solvent, or elution from or retention on an ion exchange resin. Suitable metal salts include the sodium, potassium, calcium, barium, magnesium, aluminum, and zinc salts. Similarly, the ammonium and amine salts are also considered part of the invention, these salts being prepared in substantially the same way as the metal salts from appropriate starting materials. Ammonia, ammonium hydroxide, ammonium salts, various amines, amine salts or quaternary ammonium salts and hydroxides may be employed as reactants. Suitable types of amines include:

(a) primary, secondary or tertiary alkyl and alkenyl amines having from 1 to 22 carbon atoms and up to 3 carbon-carbon double bonds;
(b) hydroxy substituted primary, secondary, and tertiary alkyl amines having from 1 to 22 carbon atoms and up to 3 hydroxyl groups;
(c) the alkylenediamines having from 1 to 6 carbon atoms; and
(d) the heterocyclic amines having from 3 to 10 carbon atoms and from 1 to 3 heteroatoms of which at least one is nitrogen.

Preferred amine salts are those of the alkyl amines having up to 6 carbon atoms or hydroxy substituted alkyl amines having up to 6 carbon atoms and 3 hydroxyl groups and the alkylenediamines having 2 to 4 carbon atoms. Suitable amines include ethylenediamine, triethylamine, tris(2-hydroxyethyl)amine, 2-hydroxyethylamine, piperidine, etc.

DETAILED DESCRIPTION OF THE INVENTION

The present invention includes a process for the production of the compounds of Formulas I which involves essentially the three steps shown in the following scheme in which $R^2$, $R^3$, Tet, W, and Y have the same meaning as above.

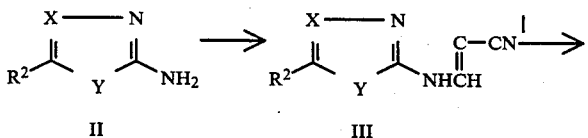

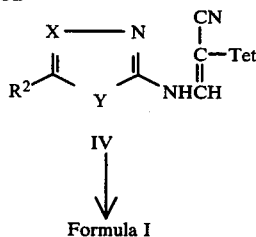

In the first step, the aminoazole of Formula II is condensed with ethoxymethylenemalononitrile to give the azolylaminomethylenepropanedinitrile of Formula III. This step is carried out under conventional conditions for the condensation of ethoxymethylenemalononitrile with an aromatic amine such as by heating in solution in a polar organic solvent such as a lower alkanol including methanol, ethanol, propanol, and butanol in the presence of a strong base such as a sodium alkoxide including sodium methoxide, sodium ethoxide, sodium propoxide, and sodium butoxide, or sodium hydride, or sodium amide.

In the second step, one of the nitrile groups of the propanedinitrile of Formula III is converted to the tetrazole group, again under conventional conditions such as treatment with ammonium chloride and sodium azide in a reaction inert organic solvent such as dimethylformamide or other suitable solvent or with aluminum azide in tetrahydrofuran. In most instances, this results in the formation of an azolylaminotetrazolylpropenenitrile of Formula IV which is then cyclized to a product of Formula I by treatment with acid. In some instances, the intermediate of Formula IV is not isolated but rather cyclization occurs to give a compound of Formula Ia or Ib wherein Z is NH.

The preferred conditions for the transformation of the intermediate of Formula IV into a product of Formula I wherein Z is oxygen involve heating the compound of Formula IV in concentrated sulphuric acid followed by the addition of water to the reaction mixture. Other acidic conditions such as the treatment of the substance of Formula IV with ethanolic HCl or with concentrated hydrobromic acid (48%) in the presence of trifluoroacetic acid may be employed. The latter two conditions generally yield a substance of Formula I wherein Z is NH which may then be transformed to the substance of Formula I wherein Z is O by hydrolysis.

To sum up, the present invention provides a process for the production of the compounds of Formula I which involves condensation of an aminoazole of Formula II with ethoxymethylenemalanonitrile under anhydrous conditions in the presence of a strong base to yield an azolylaminomethylenepropanedinitrile of Formula III, conversion of the latter by treatment with sodium azide and ammonium chloride or aluminum azide to the tetrazolylnitrile of Formula IV, or directly to the compound of Formula I wherein Z is NH, and treatment of the tetrazolylnitrile of Formula IV with strong acid to yield a compound of Formula I. When a compound of Formula I wherein Z is NH is obtained rather than the tetrazolylnitrile of Formula IV, it may be employed as such or hydrolyzed to a compound of Formula I wherein Z is O by heating with concentrated sulphuric acid followed by the addition of water to the reaction mixture. The latter hydrolysis conditions are also suitable for conversion of the tetrazolylnitrile of Formula IV to a compound of Formula I wherein Z is O.

For the preparation of those substances of Formula I wherein Z is sulphur, a substance of Formula I wherein Z is oxygen is treated under reaction conditions known for the transformation of a carboxamide or ketone into a thiocarboxamide or a thione. One suitable method is by heating the oxo compound with phosphorus pentasulfide preferably in the presence of pyridine as reaction medium.

The new compound of Formulas III and IV are also considered part of the present invention since they are useful as intermediates for the production of the substances of Formula I. Some of the substances of Formulas III and IV also have biological utility in addition to their utility as intermediates. The product of Example 5 (a compound of Formula III) possesses substantial tracheal relaxant action when measured in vitro. It is 13.2 times as potent as theophylline in relaxing the spontaneous tonus of the isolated guinea pig tracheal spiral. The intermediates of Formula IV produced in Examples 14 and 17 have antiallergic activity similar to those substances of Formula I. In the passitve cutaneous anaphylaxis test in rats described above, the substance of Example 14 exhibits an $ED_{50}$ of 32 mg./kg. and the product of Example 17 exerts 36.7% inhibition of the PCA reaction in the rat at a dose of 25 mg./kg. In both instances, the drug was administered orally.

DESCRIPTION OF SPECIFIC EMBODIMENTS

In the following examples temperatures are expressed in degrees Centigrade. Melting points are corrected values according to the USP method where indicated (corr.). The nuclear magnetic resonance (NMR) spectral characteristics refer to chemical shifts (δ) expressed as parts per million (ppm) versus tetramethylsilane as reference standard. The relative area reported for the various shifts corresponds to the number of hydrogen atoms in the individual substituent and the nature of the shift as to multiplicity is reported as broad singlet (bs), singlet (s), multiplet (m), doublet (d), triplet (t), or quadruplet (q) with coupling constant reported where appropriate. The format is NMR (solvent): δ(relative area, multiplicity, J. value, and, in some instances, indicated structural characteristics). Abbreviations employed are EtOH (ethanol), HOAc (acetic acid), Ar (aromatic group), Et$_2$O (ethyl ether), DMF (dimethylformamide), MeOH (methanol), i-PrOH (isopropanol), (EtO)$_3$CH (ethyl orthoformate), Nujol (mineral oil), DMSO-d$_6$ (deuterodimethylsulfoxide), IR (infrared), KBr (potassium bromide), EtOAc (ethyl acetate), d (decomposition), TLC (thin layer chromatography). Others are common and have well established meanings. The infrared spectra described include only absorption wave numbers (cm$^{-1}$) having functional group identification value. Structural characteristics are noted in some instances. Unless indicated otherwise, KBr was employed as diluent for IR spectral determinations.

EXAMPLE 1

2-[(5,7-Dimethylbenzothiazol-2-ylimino)methylene]-propanedinitrile

2-Amino-5,7-dimethylbenzothiazole was prepared by treatment of 3,5-dimethylaniline with ammonium thiocyanate and conversion of the resulting N-(3,5-dimethylphenyl)thiourea with bromine and chloroform (Barnikow and Bodeker Ber. 100(5), 1394), m.p. 142°–144°. 2-Amino-5,7-dimethylbenzothiazole, 6.16 g. (34.5 millimoles) was added to a solution of a pea-sized piece of sodium in 40 ml. of anhydrous ethanol. Ethoxymethylenemalononitrile, 4.22 g. (34.5 millimoles), was added to the solution and the mixture was heated at reflux for about 2 hrs. The precipitated solid was collected by filtration, washed with ethanol, and dried in vacuo at 100°, yielding 6.93 g. (72.7%) of the desired product which was a yellow solid, m.p. 239°–241°. A small portion was recrystallized from 95% ethanol and submitted for analysis, m.p. 241°–243°.

Analyses for carbon, hydrogen, and nitrogen confirmed the formula $C_{13}H_{10}N_4S$.

Various aminoazoles as shown in Examples 2–11 were substituted in the procedure of Example 1 with the production of the products listed.

EXAMPLE 2

2-Aminobenzothiazole yields 2-[(benzothiazol-2-ylamino)methylene]propenedinitrile; yield 67%, m.p. 186°–187° without recrystallization. Analysis for carbon, hydrogen, and nitrogen confirmed the formula $C_{11}H_6N_4S$.

EXAMPLE 3

3-Amino-4H-1,2,4,-triazole yields 2-[[(4H-1,2,4-triazol-3-yl)amino]methylene]propenedinitrile, yield 88%, recrystallized from 1:3 IPA/DMF, m.p. 295.0°–302.5° dec. Analyses for carbon, hydrogen, and nitrogen confirmed the formula $C_6H_4N_6$.

EXAMPLE 4

2-Amino-6-nitrobenzothiazole yields 2-[[(6-nitrobenzothiazol-2-yl)amino]methylene]propanedinitrile, yield 45%, recrystallized from acetonitrile, m.p. 249.5°–251.5°. Analyses for carbon, hydrogen, nitrogen and sulphur confirmed the formula $C_{11}H_5N_5O_2S$.

EXAMPLE 5

2-Amino-4-methylthiazole yields 2-[[(4-methylthiazol-2-yl)amino]methylene]propanedinitrile, yield 82.6%, recrystallized from acetonitrile, m.p. 184.5°–188.5° C. Analyses for carbon, hydrogen, nitrogen and sulphur confirmed the formula $C_8H_6N_4S$.

EXAMPLE 6

2-Amino-4-phenylthiazole yields 2-[[(4-phenylthiazol-2-yl)amino]methylene]propanedinitrile, yield 76.6%, recrystallized from acetonitrile, m.p. 226°–228° dec. Analyses for carbon, hydrogen, and nitrogen confirmed the formula $C_{13}H_8N_4S$.

EXAMPLE 7

2-Amino-5,6-dihydro-4H-cyclopentathiazole yields 2-[[(5,6-dihydro-4H-cyclopentathiazol-2-yl)amino]methylene]propanedinitrile; yield 73%, recrystallized from acetonitrile, m.p. 189.0°–192.0° dec. Analyses for carbon, hydrogen, and nitrogen confirmed the formula $C_{10}H_8N_4S$.

EXAMPLE 8

2-Amino-6-methoxybenzothiazole yields 2-[(6-methoxybenzothiazol-2-ylamino)methylene]-propanedinitrile, yield 57%, recrystallized from acetonitrile, m.p. 189°–190°. Analyses for carbon, hydrogen, and nitrogen confirmed the formula $C_{14}H_{12}N_2O_4S$.

EXAMPLE 9

2-Amino-5,6-dimethylbenzothiazole yields 2-[(5,6-dimethylbenzothiazol-2-ylamino)methylene]propanedinitrile, yield 43%, recrystallized from acetonitrile, m.p. 231°.

EXAMPLE 10

2-Amino-5-methoxybenzothiazole, prepared from N-(3-methoxyphenyl)thiourea by treatment with bromine in chloroform solution, yields 2-[(5-methoxybenzothiozol-2-ylimino)methylene]propanedinitrile, yield 64.8%, m.p. 238°–242°. The IR and NMR spectra confirmed the identity of the product.

EXAMPLE 11

2-Aminothiazole yields 2-[[(thiazol-2-yl)amino]methylene]propanedinitrile; yield 70%, recrystallized from isopropanol, m.p. 169°–170°.

EXAMPLE 12

N-[2-Cyano-2-(1H)tetrazol-5-yl)ethenyl]-5,7-dimethylbenzothiazol-2-amine

The propanedinitrile intermediate produced in Example 1, sodium azide, and ammonium chloride were allowed to react under the following conditions; 0.0216 mole of each of the three reactants was dissolved in 35 ml. of dimethylformamide and heated at 80° C. for 16 hrs. The mixture was then cooled to room temperature and diluted with an equal volume of water resulting in the formation of a solid precipitate. The precipitate was redissolved by adding 1N sodium hydroxide to the mixture and the solution was filtered. It was then poured into sufficient 3N hydrochloric acid to render the resulting mixture acidic and the product was collected by filtration, the yield was quantitative. A small portion was recrystallized from dimethylformamide/acetonitrile, m.p. 250°–253° C. The analyses for carbon, hydrogen, and nitrogen corresponded to the monohydrate of the desired product having the formula $C_{13}H_{11}N_7S.H_2O$.

The intermediates produced in Examples 2–11 are converted in a fashion similar to that of Example 12 to yield, respectively, products identified in Examples 13–22. Substantially quantitative yields are obtained, and generally the products are suitable for further conversion without recrystallization.

EXAMPLE 13

3-[(5-Methoxybenzothiazol-2-yl)amino]-2-(1H-tetrazol-5-yl)-2-propenenitrile for Example 10 product.

EXAMPLE 14

N-[2-Cyano-2-(1H-tetrazol-5-yl)ethenyl]benzothiazol-2-amine from Example 2 product; recrystallized from isopropanol, m.p. 263.0°–265.0° C. dec. Analyses for carbon, hydrogen, and nitrogen correspond to the quarter hydrate of the desired product having the formula $C_{11}H_7N_7S.1/4H_2O$. The CN absorption band was present in the infrared spectrum which is confirmatory of the structure assigned.

EXAMPLE 15

3,7-Dihydro-6-(1H-tetrazol-5-yl)-s-triazolo[1,5-a]pyrimidin-7-imine

The method of Example 12 when applied to the product of Example 3 yielded the imino(tetrazolyl)pyrimidine rather than the expected (tetrazolyl)propenenitrile analogous to that obtained in Example 12, m.p. softens at 216°–217° with slight decomposition and then resolidifies, fails to melt at 360°. Analyses for carbon, hydrogen, and nitrogen confirmed the formula $C_6H_5N_9$ and the infrared spectrum was confirmatory of the pyrimidine structure by virtue of the absence of absorption in the infrared corresponding to the CN group.

EXAMPLE 16

N-[2-Cyano-2-(1H-tetrazol-5-yl)ethenyl]-6-nitrobenzothiazol-2-amine from Example 4 product; 66% yield, recrystallized from dimethylformamide, m.p. 189°–192°. The presence of the CN absorption band in the infrared confirmed the assigned structure.

EXAMPLE 17

3-[(4-Methylthiazol-2-yl)amino]-2-(1H-tetrazol-5-yl)-2-propenenitrile from Example 5 product; yellow solid, m.p. darkens at 245°–280° without melting. The presence of the CN absorption band in the infrared confirmed the assigned structure.

EXAMPLE 18

3-[(4-Phenylthiazol-2-yl)amino]-2-(1H-tetrazol-5-yl)-2-propenenitrile from Example 6 product; m.p. 198°–200°. Analyses for carbon, hydrogen, and nitrogen confirmed the formula $C_{13}H_9N_7S$. The presence of the CN absorption band in the infrared confirmed the assigned structure.

EXAMPLE 19

3-[(5,6-Dihydro-4H-cyclopentathiazol-2-yl)amino]-2-(1H-tetrazol-5-yl)-2-propenenitrile from Example 7 product.

EXAMPLE 20

N-[2-Cyano-2-(1H-tetrazol-5-yl)ethenyl]-6-methoxybenzothiazol-2-amine from Example 8 product; dark yellow solid, m.p. 231°–235° dec.

EXAMPLE 21

N-[2-Cyano-2-(1H-tetrazol-2-yl)ethenyl]-5,6-dimethylbenzothiazol-2-amine from Example 9 product; m.p. 224°–228° dec. The infrared absorption spectrum indicated the presence of $H_2O$ (product is a hydrate) but confirmed the structure by the presence of the CN band.

EXAMPLE 22

6-(1H-Tetrazol-5-yl)-5H-thiazole[3,2-a]pyrimidine-5-imine.

When the method of Example 12 was applied to the product of Example 11, the product which was obtained in 40% yield did not contain the CN absorption band in the infrared spectrum. It was purified by dissolving in aqueous potassium carbonate and reprecipitating with acetic acid, m.p. in excess of 350°. Elemental analysis for carbon, hydrogen, and nitrogen confirmed that the assigned structure with the product being obtained as the monohydrate having the formula $C_7H_5N_7S.H_2O$.

EXAMPLE 23

3-(1H-Tetrazol-5-yl)-4H-pyrimido[2,1-b]-benzothiazol-4-imine Hydrochloride

The product of Example 14, 3 g (0.011 mole) was dissolved in 50 ml. of 2N hydrogen chloride in anhydrous ethanol and the mixture was heated at reflux for 4 hrs. during which time a yellow precipitate formed. The mixture was cooled to room temperature and the product collected by filtration, yield 1.9 g. (60%), recrystallized from dimethylformamide, m.p. 274.0°–275.0° dec. Analyses for carbon, hydrogen, and nitrogen confirmed the formula $C_{11}H_7N_7S \cdot HCl$.

EXAMPLE 24

3-(1H-Tetrazol-5-yl)-4H-pyrimido[2,1-b]benzothiazol-4-one

The product of Example 14, 350 mg. (0.0013 mole) was dissolved with heating in about 10 ml. of 48% aqueous hydrobromic acid to which 5 ml. of trifluoroacetic acid was added. After about 20 min. a yellow precipitate formed which was collected and dried, m.p. 328°–329° dec. Analyses for carbon, hydrogen, and nitrogen corresponded to the hemihydrate having the formula $C_{11}H_6N_6OS \cdot \frac{1}{2}H_2O$. This product was also obtained, this time in anhydrous form, by hydrolysis of the product of Example 23, 0.11 mole, by heating on the steam bath for 20 min. with 100 ml. of trifluoroacetic acid and 20 ml. of 48% aqueous hydrobromic acid. The addition of water, 50 ml., and chilling of the mixture resulted in the precipitation of 11.6 g of 3-(1H-tetrazol-5-yl)-4H-pyrimido[2,1-b]benzothiazol-4-imine hydrobromide which was separated by filtration. The filtrate was concentrated by distillation which resulted in crystallization of the desired product, yield 2 g. (7%), which was recrystallized from dimethylformamide as a light yellow solid, m.p. 317.0°–318.0° dec. Analyses for carbon, hydrogen, and nitrogen confirmed the formula $C_{11}H_6N_6OS$.

EXAMPLE 25

7,9-Dimethyl-3-(1H-tetrazol-5-yl)-4H-pyrimido[2,1-b]benzothiazol-4-one

The product of Example 12, 7 g. was cautiously added to 21 ml. of concentrated sulphuric acid. Considerably frothing occurred and, after the reaction subsided, the mixture was heated at 100° for 15 min. Water, 7 ml. was then carefully added and heating was continued for an additional 15 min. The mixture was then diluted with several volumes of water and the precipitated solid was collected by filtration. The product was recrystallized from dimethylformamide/acetonitrile yielding 2.35 g. of a dark tan solid, m.p. 293°–295° dec. Analysis for carbon, hydrogen, and nitrogen corresponded to the formula $C_{13}H_{10}N_6OS$.

The methods of Procedure 25 is applied to the intermediates of Examples 13 and 16–22 to yield the products identified in Examples 26–33.

EXAMPLE 26

7-Methoxy-3-(1H-tetrazol-5-yl)-4H-pyrimido[2,1-b]benzothiazol-4-one

This product is prepared from the products of Example 13 by the method of Example 25.

EXAMPLE 27

8-Nitro-3-(1H-tetrazol-5-yl)-4H-pyrimido[2,1-b]-benzothiazol-4-one

The product of Example 16 is converted to this product by the method of Example 25, m.p. 308°–310° dec. without recrystallization, yield 73.8%. Elemental analyses for carbon, hydrogen, and nitrogen confirmed that the product was obtained as the sesquihydrate having the formula $C_{11}H_5N_7O_3S \cdot 1\frac{1}{2}H_2O$. The infrared spectrum and mass spectral analysis were in agreement with the structure given.

EXAMPLE 28

3-Methyl-6-(1H-tetrazol-5-yl)-5H-thiazolo[3,2-a]pyrimidine-5-one

This material was produced from the product produced in Example 17 by the method of Example 25, yield 90.6%, recrystallized from dimethylformamide, m.p. 316.0°–319.0° dec. Analyses for carbon, hydrogen, and nitrogen and sulphur confirmed the formula $C_8H_6N_6OS$. The infrared and nuclear magnetic resonance spectrum also confirmed the structure assigned.

EXAMPLE 29

3-Phenyl-6-(1H-tetrazol-5-yl)-5H-thiazolo[3,2-a]pyrimidin-5-one

Application of the method of Example 25 to the product of Example 18 yields this substance, yield 69%, m.p. 258°–262° dec. The infrared absorption spectrum confirmed the structure assigned.

EXAMPLE 30

3-(1H-Tetrazol-5-yl)-4H-pyrimido[2,1-b]-(5,6-dihydro-4H-cyclopentathiazole)

This material is produced by application of the method of Example 25 to the product of Example 19.

EXAMPLE 31

8-Methoxy-3-(1H-tetrazol-5-yl)-4H-pyrimido[2,1-b]benzothiazol-4-one

The product of Example 20 was cyclized according to the method of Example 25 to yield this product, yield 46%, failed to melt at 300° C. Elemental analysis for carbon, hydrogen, and nitrogen confirmed the formula $C_{12}H_8N_6O_2S$ and the infrared also confirmed the structure assigned.

EXAMPLE 32

7,8-Dimethyl-3-(1H-tetrazol-5-yl)-4H-pyrimido[2,1-b]benzothiazol-4-one

The method of Example 25 when applied to the product of Example 21 yields this substance, yield 92.6%, recrystallized from dimethylformamide, m.p. 328.0°–346.0° dec. The elemental analysis confirmed the formula $C_{13}H_{10}N_6OS$ and the infrared absorption spectrum was consistent with the structure assigned.

EXAMPLE 33

6-(1H-Tetrazol-5-yl)-5H-thiazolo[3,2-a]pyrimidin-5-one

The method of Example 25 is applied to the product of Example 22 to yield this substance. It was obtained in 77.2% yield, twice recrystallized from dimethylformamide, m.p. 336.0–338.0 dec.

Anal. Calcd. for $C_7H_4N_6OS$: C, 38.18; H, 1.83; N, 38.16. Found: C, 38.57; H, 2.43; N, 37.95.

EXAMPLE 34

3-(1H-Tetrazol-5-yl)-4H-pyrimido[2,1-b]benzothiazol-4-one Potassium Salt

A solution of 2.44 g. (0.037 mole) of potassium hydroxide in 200 ml. of methanol was prepared and warmed on the steam bath. The product of Example 24, 0.037 mole, was added thereto. The latter did not dissolve but formed clumps which gradually turned into a white precipitate as heating and stirring was continued. The mixture was then cooled to room temperature and the precipitate collected, yield 7.57 g, m.p. 338°–340° dec. This material was recrystallized from methanol, m.p. 336.0–339.0 dec. Analyses for carbon, hydrogen, nitrogen, and sulphur corresponded to the sesquihydrate having the formula $C_{11}H_5N_6OS.K.1\frac{1}{2}H_2O$. The nuclear magnetic resonance and infrared spectrum were characteristic of the assigned structure.

EXAMPLE 35

3-(1H-Tetrazol-5-yl)-4H-pyrimido[2,1-b]benzothiazol-4-thione

The product of Example 24, 0.02 mole, and 12.0 g. (0.054 mole) of $P_2S_5$ in 125 ml. of pyridine is heated at reflux for 5 hrs. and then poured into 1 l. of ice and water mixture. The product is collected by filtration, the solid dissolved in dilute NaOH, treated with decolorizing carbon, filtered and the filtrate acidified whereupon the purified product precipitated and was collected on a filter.

Spectral data for a number of the products of the foregoing examples are arranged in the following table.

TABLE I

| | SPECTRAL DATA | |
|---|---|---|
| Example | NMR | IR |
| 5 | (DMSO-$d_6$) 2.82 (3, m) 7.35 (1 m), 8.26 (1, s) | 780, 1075, 1280, 1350, 1490, 1550, 1640, 2220, 3100, 3300 |
| 14 | (DMSO-$d_6$) 7.90 (4, m) 8.62 (1, s), 11.20 (s, bs) | 760, 1280, 1470, 1530, 1560, 1645, 2235, 3080, 3170 |
| 15 | (DMSO-$d_6$) 8.66 (1, s), 9.02 (1, s), 9.10 (2, bs) | 780, 1150, 1200, 1340, 1480, 1540, 1610, 1650, 2500, 3300 |
| 17 | (DMSO-$d_6$) 2.27 (3, m), 6.80 (1, m), 8.29 (1, s) 8.73 (1, bs) | 750, 1050, 1330, 1450, 1540, 1570, 1580, 1650, 2220, 3090 |
| 22 | ($CF_3COOH$) 8.30 (1, d, 5.0 Hz), 8.81 (1, d, 5.0 Hz) 9.82 (1, s) | 720, 760, 1055, 1320, 1520, 1590, 1695, 3070, 3130 |
| 23 | (DMSO-$d_6$) 8.00 (2, m) 8.61 (2, m), 9.49 (1, s) | 770, 1280, 1340, 1510, 1568, 1590, 1645, 2690, 3110 |
| 24 (anhydrous) | ($CF_3COOH$) 8.12 (3, m) 9.40 (m, 1), 9.62 (1, s) | 782, 1000, 1260, 1340, 1500, 1540, 1590, 1675, 3140 |
| 25 | (DMSO-$d_6$) 2.47 (6, s) 7.31 (1, s), 8.66 (1, s) 8.88 (1, s) | 780, 1040, 1305, 1340, 1500, 1530, 1670, 3170 |
| 28 | ($CF_3COOH$) 3.10 (3, m) 7.34 (1, m), 9.47 (1, s) | 780, 1030, 1340, 1410, 1485, 1580, 1690, 3120 |
| 31 | ($CF_3COOH$) 4.10 (3, s) 7.67 (2, m), 9.30 (1, m) | 775, 1050, 1160, 1280, 1340, 1510, 1600, 1665, 3130 |
| 32 | Sample insoluble | 775, 1030, 1280, 1330, 1495, 1530, |

TABLE I-continued

| | SPECTRAL DATA | |
|---|---|---|
| Example | NMR | IR |
| 33 | ($CF_3COOH$) 8.05 (1, d, 5.0 Hz) 8.72 (1, d, 5.0 Hz) 9.68 (1, s) | 1580, 1670, 3110 750, 825, 1040, 1300, 1350, 1485, 1530, 1580, 1680, 3120 |
| 34 | ($D_2O$ with HDO = 4.80 ppm as reference) 7.2 (3, m) 7.89 (1, s), 8.20 (1, m) | 780, 1000, 1250, 1325, 1440, 1520, 1650, 3430 |

The methods of Examples 1, 12 and 25 are applied to the thiazoles listed in Table II for the preparation of the substances of Formula Ia depicted in the table.

TABLE II

Additional Products of Formula Ia

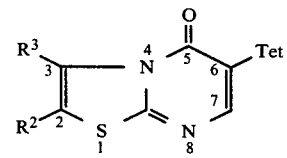

| Example No. | Thiazole Starting Material | Product ($R^2$, $R^3$) |
|---|---|---|
| 36 | 2-amino-5-octylthiazole* | 2-octyl, H |
| 37 | 2-amino-4,5-dimethylthiazole* | 2,3-dimethyl |
| 38 | 2-amino-4,5,6,7-tetrahydrocyclohexathiazole* | 2,3-tetramethylene |
| 39 | 2-amino-5-ethenyl-4-methylthiazole* | 2-ethenyl-3-methyl |
| 40 | 2-amino-5-ethinyl-4-methylthiazole* | 2-ethinyl-3-methyl |
| 41 | 2-amino-4-methyl-5-phenyl thiazole* | 3-methyl-2-phenyl |
| 42 | 2-amino-4-methyl-5-(phenylmethyl) thiazole* | 3-methyl-2-(phenyl-methyl) |
| 43 | 2-amino-4-methyl-5-sulfothiazole+ | 2-sulfo-3-methyl |
| 44 | 2-amino-5-bromo-4-methylthiazole+ | 2-bromo-3-methyl |
| 45 | 2-amino-4-methyl-5-nitrothiazole+ | 2-nitro-3-methyl |
| 46 | 2,5-diamino-4-methylthiazole** | 2-amino-3-methyl |
| 47 | 2-amino-5-hydroxy-4-methylthiazole++ | 2-hydroxy-3-methyl |
| 48 | 2-amino-5-methoxy-4-methylthiazole++ | 2-methoxy-3-methyl |
| 49 | 2-amino-5-iodo-4-methylthiazole++ | 2-iodo-3-methyl |
| 50 | 2-amino-5-(isopropylthio)-4-methylthiazole++ | 2-(isopropylthio)-3-methyl |
| 51 | 2-amino-5-(2-buten-1-yl)thiazole | 2-(2-buten-1-yl) |
| 52 | 2-amino-4-(cyclohexylmethyl)thiazole | 3-cyclohexylmethyl |
| 53 | 2-amino-5-cyanomethylthiazole | 2-$CH_2CN$, H |
| 54 | 2-amino-4-methyl-5-(methylsulfinyl)-thiazole* | 2-(methylsulfinyl)-3-methyl |
| 55 | 2-amino-4-methyl-5-(methylsulfonyl)-thiazole* | 2-(methylsulfonyl)-3-methyl |
| 56 | 5-acetylamino-2-amino-4-methyl-thiazole* | 2-(acetylamino)-3-methyl |
| 57 | 2-amino-5-carbamoyl-4-methyl-thiazole* | 2-carbamoyl-3-methyl |
| 58 | 2-amino-5-cyano-4-methylthiazole* | 2-cyano-3-methyl |
| 59 | 2-amino-5-ethoxycarbonyl-4-methyl- | 2-ethoxycarbonyl- |

TABLE II-continued
Additional Products of Formula Ia

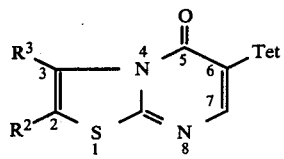

| Example No. | Thiazole Starting Material | Product ($R^2$, $R^3$) |
|---|---|---|
| | thiazole* | 3-methyl |

*Prepared according to the methods of Tartell, et al., J. Amer. Chem. Soc., 72, 3138 (1950), or Byers, et al., Org. Syn. Coll. Vol. 3, 332 (1955), or modifications thereof.
+Preparable from 2-amino-4-methylthiazole by standard electrophilic sulfonation, halogenation, or nitration methods.
**Preparable by the catalytic hydrogenation of 2-amino-4-methyl-5-nitrothiazole.
++2-Amino-4-methylthiazole may be acetylated to yield 2-acetylamino-4-methylthiazole and the latter diazotized. The resulting diazonium salt may be converted to the indicated starting materials by known methods. The 2-acetylamino group is then hydrolyzed to yield the indicated 2-aminothiazole starting material.

The methods of Examples 1, 12, and 25 are applied to the benzothiazoles listed in Table III for the preparation of the substances of Formula V which are identified in that table.

TABLE III
Additional Products of Formula V

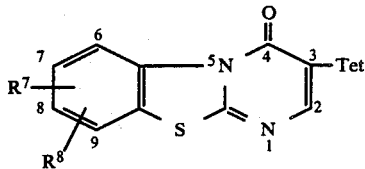

| Example No. | Benzothiazole Starting Material | Product ($R^7$, $R^8$) |
|---|---|---|
| 60 | 2-amino-4-methylbenzothiazole | 6-$CH_3$, H, H |
| 61 | 2-amino-5-methylbenzothiazole | 7-$CH_3$, H |
| 62 | 2-amino-6-methylbenzothiazole | 8-$CH_3$, H |
| 63 | 2-amino-7-methylbenzothiazole | 9-$CH_3$, H |
| 64 | 2-amino-5,6-dimethoxybenzothiazole | 7,8-dimethoxy |
| 65 | 2-amino-4-chlorobenzothiazole | 6-chloro, H |
| 66 | 2-diaminobenzothiazole | 6-$NH_2$, H |
| 67 | 6-acetylamino-2-amino-benzothiazole | 8-$CH_3CONH$, H |
| 68 | 2-amino-6-cyanobenzothiazole | 8-CN, H |
| 69 | 2-amino-6-carbamoylbenzothiazole | 8-$NH_2CO$, H |
| 70 | 2-amino-6-ethoxycarbonylbenzothiazole | 8-$CO_2C_2H_5$, H |
| 71 | 2-amino-6-methylthiobenzothiazole | 8-$CH_3S$, H |
| 72 | 2-amino-6-(methylsulfinyl)benzothiazole | 8-$CH_3SO$, H |
| 73 | 2-amino-6-methylsulfonylbenzothiazole | 8-$CH_3SO_2$, H |
| 74 | 2-amino-6-sulfobenzothiazole+ | 8-$SO_3H$, H |
| 75 | 2-amino-5-ethenylbenzothiazole | 7-$CH_2$=CH, H |
| 76 | 2-amino-4-acetylbenzothiazole | 6-$CH_3CO$, H |
| 77 | 2-amino-5-alkyloxybenzothiazole | 7-$CH_2$=$CHCH_2O$, H |
| 78 | 2-amino-6-(cyclopropylmethyl)benzothiazole | 8- ▷—$CH_2$, H |
| 79 | 2-amino-4-(ethylcyclopropyl)benzothiazole | 6-$C_2H_5$—△ |
| 80 | 2-amino-5-ethinylbenzothiazole | 7-HC≡C, H |
| 81 | 2-amino-5-phenylbenzothiazole | 7-$C_6H_5$, H |
| 82 | 2-amino-5-(phenylmethyl) benzothiazole | 7-$C_6H_5CH_2$ |

TABLE III-continued
Additional Products of Formula V

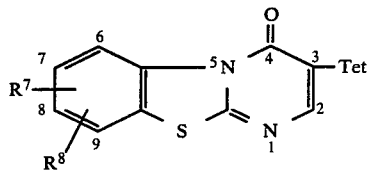

| Example No. | Benzothiazole Starting Material | Product ($R^7$, $R^8$) |
|---|---|---|
| 83 | 2-amino-5-trifluoromethylbenzothiazole | 7-$CF_3$, H |
| 84 | 2-amino-6-trifluoromethylbenzothiazole | 8-$CF_3$, H |

*Preparable by the method of Barnikow, et al., Ber, 100(5), 1394, (1967).
+Prepared by sulfonation of 2-acetylaminobenzothiazole and hydrolysis of the acetylamino group.

EXAMPLE 85

2-[(Benzimidazol-2-ylimino)methylene]propanedinitrile

This intermediate is obtained by condensation of 2-aminobenzimidazole and ethoxymethylenemalononitrile according to the method of Example 1, yield 91%. The identity of the product was confirmed by the character of the IR and NMR spectra, m.p. 320°-325° (shrinks at 290°). TLC on silica, $CHCl_3$/MeOH 3:1 $R_f$ 0.8.

EXAMPLE 86

N-[2-Cyano-2-(1H)-tetrazol-5-yl)ethenyl]benzimidazol-2-amine

Application of method of Example 12 to the product of Example 85 yielded this product, yield 75%, m.p. 340°-345° d. (blackens at 300°). Identity was confirmed by IR.

EXAMPLE 87

3-(1H-Tetrazol-5-yl)-4H-pyrimido[1,2-a]benzimidazol-4-one

This product was produced from the product of Example 86 by the sulfuric acid cyclization method of Example 25, yield 53%, m.p. 323°-324° d. The product was identified by IR.

EXAMPLE 88

Preparative Scale Method for 3-(1H-Tetrazol-5-yl)-4H-pyrimido[2,1-b]benzothiazol-4-one The product of Example 14, 243.0 gm. (0.903 mole) in 600 ml. concentrated sulfuric acid was mechanically stirred and heated at 95° C. for 1 hr. The reaction mixture was cooled to room temperature, diluted with 230 ml. of ice water, then reheated at 95° for 2 hrs. After cooling, 600 ml. of water was added and the mixture allowed to stand overnight. The precipitate was collected by filtration, washed with water and dried to afford 153.3 gm. (62.8%) of product identical with the anhydrous material described in Example 24.

For the preparation of pharmaceutical compositions containing the compounds of Formula I in the form of dosage units for oral administration, the compound is mixed with a solid, pulverulent carrier such as lactose, sucrose, sorbitol, mannitol, potato starch, corn starch, amylopectin, cellulose derivatives, or gelatin, as well as with glidents such as magnesium stearate, calcium stearate, polyethylene glycol waxes or the like and compressed into tablets. The tablets may be used uncoated or coated by known techniques.

In the preparation of soft gelatin capsules comprised of a shell made of gelatin and glycerine or the like, the active ingredient is mixed with a vegetable oil and encapsulated in conventional manner. Hard gelatin capsules may contain granules of the active ingredient in combination with a solid, pulverulent carrier such as lactose, sucrose, sorbitol, mannitol, starch (such as e.g. potato starch, corn starch, or amylpectin), cellulose derivatives or gelatin.

Dose units for rectal administration may be prepared in the form of suppositories containing the compound in a mixture with a neutral fat base, or in the form of a gelatin-rectal capsule with a mixture of vegetable oil or paraffin oil.

Liquid preparations suitable for oral administration are suspensions, syrups and elixirs containing from about 0.2% by weight to about 20% by weight of the active ingredient.

A suitable injectible composition comprises an aqueous solution of a water soluble pharmaceutically acceptable salt adjusted to physiologically acceptable pH.

EXAMPLE 89

Tablets for Oral Ingestion

The following ingredients are blended in the dry state in a twin-shell blender and compressed on a tablet press using an 11/32 inch die and concave punches.

| Product of Example 88, anhydrous | 50.0 g. |
|---|---|
| Sucrose pregranulated for direct compression | 210.0 g. |
| Corn starch | 6.0 g. |
| Microcrystalline cellulose | 40.0 g. |
| Magnesium stearate | 1.0 g. |

This batch size is for 1,000 tablets and provides a tablet weighing 307 mg. supplying 50 mg. of active ingredient per tablet. Tablets containing from 25-200 mg. may be made employing the same ingredients, but adjusting the weight and tablet size appropriately.

EXAMPLE 90

Powder for Inhalation

The following ingredients are blended aseptically and filled into hard gelatin capsules, each containing 50 mg. of the mixture providing 25 mg. of the active ingredient.

| Product of Example 88, anhydrous micronized | 25.0 g. |
|---|---|
| Lactose powder | 25.0 g. |

The foregoing is sufficient for 1,000 capsules. These capsules are suitable for dispensing the powder into the inspired air stream using a breath actuated device. Appropriate adjustments of the composition can be made to give capsules containing 0.5–40 mg. of active ingredient.

What is claimed is:

1. A compound selected from the group consisting of a compound of Formula IV

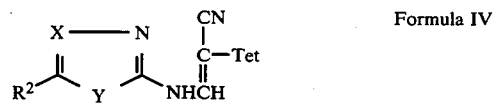

Formula IV wherein

X is N or $CR^3$,

Y is S, or NH with the proviso that when Y is S, X is $CR^3$,

Tet is 1H-tetrazol-5-yl;

$R^2$ and $\overline{R}^3$ are independently selected from H, the substituent A, or taken together with the carbon atoms to which they are attached denote cycloalkyl or cycloalkenyl having 5 to 7 ring members and up to 2 ring substituents, benzo, mono-substituted benzo, or di-substituted benzo wherein said substituents are independently defined by A, and A is selected from the group consisting of alkyl, alkenyl, alkynyl, alkoxy, alkenoxy, alkanoyl, alkenoyl, alkylsulfonyl, alkylsulfinyl, alkylthio, alkanoamido, cycloalkyl having 3 to 6 ring members and 1 to 3 optional alkyl substituents, cycloalkylalkyl having 3 to 6 ring members and 1 to 3 optional alkyl substituents, wherein each of the foregoing groups has up to 8 carbon atoms, phenyl, phenylmethyl, trifluoromethyl, nitro, amino, hydroxyl, halogen, carbamoyl, cyano, and cyanoalkyl having from 2 to 4 carbon atoms.

2. The compound of claim 1, N-[2-cyano-2-(1H-tetrazol-5-yl)ethenyl]benzothiazol-2-amine.

3. The compound of claim 1, 3-[(4-methyl-2-thiazolyl)amino]-2-(1H-tetrazol-5-yl)-2-propenenitrile.

4. The method of inhibiting the immediate hypersensitivity reaction in a sensitive mammal which comprises administering to said mammal a non-toxic effective hypersensitivity reaction inhibiting dose of a compound claimed in claims 2 or 3.

* * * * *